(12) United States Patent
Hooker et al.

(10) Patent No.: US 8,030,526 B2
(45) Date of Patent: Oct. 4, 2011

(54) SIMPLE, RAPID METHOD FOR THE PREPARATION OF ISOTOPICALLY LABELED FORMALDEHYDE

(75) Inventors: Jacob Matthew Hooker, Port Jefferson, NY (US); Matthias Schonberger, Mains (DE); Hanno Schieferstein, Aabergen (DE); Joanna S. Fowler, Bellport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 207 days.

(21) Appl. No.: 12/488,680

(22) Filed: Jun. 22, 2009

(65) Prior Publication Data

US 2009/0317880 A1 Dec. 24, 2009

Related U.S. Application Data

(60) Provisional application No. 61/074,191, filed on Jun. 20, 2008.

(51) Int. Cl.
C07C 45/00 (2006.01)
C07C 47/04 (2006.01)
(52) U.S. Cl. ........................................ 568/448; 568/490
(58) Field of Classification Search .................. 568/448, 568/490
See application file for complete search history.

(56) References Cited

OTHER PUBLICATIONS

Meisenheimer, J., "Regarding the Dissimilarity of the Five Valences of Nitrogen", Justus Liebigs Ann. Chem. 397:273 (1913) (German and unofficial English translation).
Fowler, J., et al., "Working against Time: Rapid Radiotracer Synthesis and Imaging the Human Brain," Acc. Chem. Res., vol. 30, No. 4 pp. 181-188 (1997).
Hooker, J.M., et al., "A Simple, Rapid Method for the Preparation of [$^{11}$C]Formaldehyde," Angew. Chem. Int. Ed., vol. 47, pp. 5989-5992 (2008).
Miller, P.W., et al., "Synthesis of $^{11}$C, $^{18}$F, $^{15}$O, and $^{13}$N Radiolabels for Positron Emission Tomography," Angew. Chem., Int. Ed., vol. 47, pp. 8998-9033 (2008).
Roeda, D., et al., "[$^{11}$C]Formaldehyde Revisited: Considerable Concurrent [$^{11}$C]formic Acid Formation in the Low-Temperature Conversion of [$^{11}$C]carbon Dioxide into [$^{11}$C]Formaldehyde," Appl. Radiat. Isot., vol. 54, pp. 935-939 (2001).
Nader, M.W., et al., "Low Temperature Synthesis of No-carrier-added [$^{11}$C]Formaldehyde with Metal Hydrides and Preparation of [1-$^{11}$C]1,2,3,4-Tetrahydro-β-Carboline Derivatives," Appl. Radiat. Isot., vol. 49, No. 12, pp. 1599-1603 (1998).
Larsen, P., et al., "Synthesis of [$^{11}$C]Iodomethane by Iodination of [$^{11}$C]Methane," Appl. Radiat. Isot., vol. 48, No. 2, pp. 153-157 (1997).
Crouzel, C., et al., "Recommendations for a Practical Production of [$^{11}$C]methyl Iodide," Appl. Radiat. Isot., vol. 38, No. 8, pp. 601-603 (1987).
Berger, G., et al., "Automated Synthesis of $^{11}$C-Labelled Radiopharmaceuticals: Imipramine, Chlorpromazine, Nicotine and Methionine," Appl. Radiat. Isot., vol. 30, pp. 393-395 and pp. 397-399 (1979).
Lodi, F., et al., "A Simple Tracelab Module Modification for Automated On-Column [$^{11}$C]methylation and [$^{11}$C]carboxylation," Appl. Radiat. Isot., vol. 65, pp. 691-695 (2007).
Slegers, et al., "Enzymatic Synthesis of C-11 Formaldehyde: Concise Communication," J. Nucl. Med., vol. 25, pp. 338-342 (1984).
Straatmann, M.G., et al., "A General Method for Labeling Proteins with $^{11}$C," J. Nucl. Med., vol. 16, No. 5, pp. 425-428 (1974).
De Munari, S., et al., "Hypervalent Iodine Oxidants: Structure and Kinetics of the Reactive Intermediates in the Oxidation of Alcohols and 1,2-Diols by O-Iodoxybenzoic Acid (IBX) and Dess-Martin Periodinane. A Comparative $^1$H-NMR Study," J. Org. Chem., vol. 61, pp. 9272-9279 (1996).
Hughes, J.A., et al., "Preparation of [$^{11}$C]formaldehyde Using a Hollow Fiber Membrane Bioreactor," Nucl. Med. Biol., vol. 22, No. 1, pp. 105-109 (1995).
Svärd, H., et al., "The Synthesis of Some $^{11}$C-Labelled Aliphatic Amino Acids," J. Labell. Comp. Radio., vol. XXI, Nos. 11-12, pp. 1175-1176 (2006).
Li, J-L., et al., "A New Silver-Containing Ceramics for Catalytic Oxidation of Methanol to Formaldehyde," Materials Letters, vol. 44, pp. 233-236 (2000).
Link, J.M., et. al., "Production of [$^{11}$C]CH$_3$I by Single Pass Reaction of [$^{11}$C]CH$_4$ with I$_2$," Nucl. Med. Biol., vol. 24, pp. 93-97 (1997).
Marazano, C., et al., "Synthesis of Methyl Iodide-$^{11}$C and Formaldehyde-$^{11}$C," Appl. Radiat. Isot., vol. 28, pp. 49-52 (1977).
Maziere, M., et al., "$^{11}$C-Clomipramine. Synthesis and Analysis," J. Radioanalyt. Chem., vol. 45, pp. 453-457 (1978).

*Primary Examiner* — Sikarl Witherspoon
(74) *Attorney, Agent, or Firm* — Dorene M. Price

(57) ABSTRACT

Isotopically labeled formaldehyde (*C$^s$H$_2$O) is prepared from labeled methyl iodide (*C$^s$H$_3$I) by reaction with an oxygen nucleophile having a pendant leaving group. The mild and efficient reaction conditions result in good yields of *C$^s$H$_2$O with little or no *C isotopic dilution. The simple, efficient production of $^{11}$CH$_2$O is described. The use of the $^{11}$CH$_2$O for the formation of positron emission tomography tracer compounds is described. The reaction can be incorporated into automated equipment available to radiochemistry laboratories. The isotopically labeled formaldehyde can be used in a variety of reactions to provide radiotracer compounds for imaging studies as well as for scintillation counting and autoradiography.

51 Claims, No Drawings

SIMPLE, RAPID METHOD FOR THE PREPARATION OF ISOTOPICALLY LABELED FORMALDEHYDE

PARENT CASE

This application claims benefit of U.S. Provisional Application No. 61/074,191 filed Jun. 20, 2008, the entire contents of which are incorporated herein by reference.

GOVERNMENT SUPPORT

This invention was made with Government support under contract number DE-AC02-98CH10886, awarded by the U.S. Department of Energy and sponsored by the National Institutes of Health under grant number 1F32EB008320-01. The Government has certain rights in the invention.

BACKGROUND OF THE INVENTION

The present invention methods and materials relate to the simple, efficient production of isotopically labeled formaldehyde for use in the formation of radiotracer compounds.

Synthesis of formaldehyde containing isotopes of carbon ($^{11}C$, $^{13}C$ and $^{14}C$, hereinafter denoted as *C) and isotopes of hydrogen (deuterium (D) and tritium (T)) are contemplated embodiments of this invention. A preferable embodiment of the present invention is the simple, efficient production of [$^{11}C$]formaldehyde ($^{11}CH_2O$) for use in the formation of $^{11}C$-labeled radiotracer compounds for positron emission tomography.

In some embodiments, the hydrogen atoms of $^{11}CH_2O$ may be replaced with deuterium ($^{11}CD_2O$) or tritium ($^{11}CT_2O$). Deuterium-substituted radiotracers can have different pharmacokinetics, which can be used to alter the utility of various radiotracer compounds (Fowler, et al. (1994) J. Nucl. Med. 36:1255). The radioactive tritium substitution of various radiotracers can be useful for validation of in vivo imaging through in vitro radiographic studies as well as for validation of serum concentrations of the radiotracer compound through scintillation counting.

Carbon-13 and carbon-14 formaldehyde can be synthesized through the methods of the invention and used for various applications. For example, $^{13}CH_2O$ may be used in place of $^{11}CH_2O$ when developing a new synthetic route for the preparation of a new radiotracer compound. $^{14}CH_2O$ can be used to incorporate radioactivity into the same radiotracer compound which can then be used to validate in vivo imaging results through the use of the carbon-14 labeled compound for in vitro autoradiography studies and through scintillation counting.

Positron emission tomography (PET) is an analytical imaging technology which utilizes compounds labeled with positron emitting radioisotopes as molecular probes to image and measure biological and biochemical processes. To image biological processes using PET, atoms in particular biological compounds are replaced or substituted with the positron emitting radioisotopic atoms to form various radiotracer compounds. Oxygen, nitrogen and carbon atoms of organic compounds can be substituted with their positron emitting isotopes ($^{15}O$, $^{13}N$ and $^{11}C$). Because there are no positron emitting isotopes of hydrogen, the positron emitting fluorine-18 ($^{18}F$) isotope is used as a substitute for hydrogen. Other, less frequently used positron emitting isotopes include those of Cu, Zn, K, Br, Rb, I, P, Fe, Ga and others. For the most typically used PET isotopes (O, N, C and F) the short half-life of the radioisotope demands that the synthetic chemical reaction incorporating the radioisotope be quick, efficient and of high yield, with little or no isotope dilution. In particular, for $^{11}C$, which has a half-life of 20.4 minutes, production of the radio-carbon through completion of the imaging scan must be accomplished in two to three hours (Fowler, et al. (1997) Acc. Chem. Res. 30:181-188). A typical preparation includes about 10 minutes for isotope production (generally in the form of $^{11}CO_2$ or $^{11}CH_4$), 40 to 60 minutes or less for radiotracer synthesis and up to about 90 minutes for PET imaging.

The incorporation of carbon-11 into small molecules has been paramount to the success of positron emission tomography for in vivo molecular imaging and drug research and development. However, many of the properties that make [$^{11}C$] an ideal radionuclide for PET have impeded its chemical development. For instance, as noted above, the short half-life ($t_{1/2}$=20.4 min) necessitates rapid chemical syntheses and purifications. Moreover, high specific activity, which makes it possible to image low concentration receptors and molecular targets, places the working concentration of [$^{11}C$] labeling reagents in the low nanomolar range. But perhaps the biggest challenge in the synthesis of [$^{11}C$]-labeled compounds is the lack of available labeling reagents.

Nearly all carbon-11 syntheses begin with a nuclear reaction [$^{14}N(p, \alpha)^{11}C$] using a cyclotron or other accelerator to produce $^{11}CO_2$ or $^{11}CH_4$ from which labeling reagents are prepared.

By far the most common, almost canonical method, to label a molecule with [$^{11}C$] is through methylation, typically with $^{11}CH_3I$, which is simply prepared using commercially available reagents and equipment (e.g., General Electric TRACERlab™ FX C Pro). While methyl groups appear quite frequently in relevant compounds and [$^{11}C$]-methylation has led to many successful radiotracers, reliance on methylation limits the range of potential radiotracer probe compounds. Consequently, there exists a need for new reaction development to focus on methods to incorporate [$^{11}C$] in skeletal positions of target molecules. Several research groups have developed or adapted synthetic methods for $^{11}C$ incorporation into benzene rings, carbocycles, and heterocycles as well as non-pendant locations. By using carefully designed synthetic organic reactions, each of these has expanded the types of radiotracers that can be accessed.

[$^{11}C$]Formaldehyde has shown great promise as a labeling reagent for the preparation of PET compounds. Due to its versatile oxidation state, [$^{11}C$]formaldehyde ($^{11}CH_2O$) provides a way to insert carbon-11 into compounds through routes that cannot be synthesized using the more readily available $^{11}CH_3I$. For example, it has been used in synthesis of a variety of compounds through reductive methylations (Straatmann et al. (1975) J. Nucl. Med. 16:425; Marazano, et al. (1977) Int. J. App. Radiat. Isot. 28:49; Maziere, et al. (1977) J. Label. Comp. Radiopharm. (1977) 28:196; Berger et al. (1979) Int. J. App. Radiat. Isot. 30:393), ring-closure reactions (Nader et al. (1998) Appl. Radiat. Isot. 49:1599; Roeda, et al. (2002) J. Label. Comp. Radiopharm. 45:37; Van der Mey, et al. (2006) Bioorg. Med. Chem. 14:4526) and electrophilic aromatic substitutions (Langer, et al. (2005) J. Label. Comp. Radiopharm. 48:577) among others (e.g., Pike et al. (1984) Int. J. Appl. Radiat. Isot. 35:103).

However, the widespread development and use of synthetic methods employing [$^{11}C$]formaldehyde in the preparation of PET-compounds has been hindered by its lack of availability to most radiochemistry facilities. Several methods have been developed for the synthesis of [$^{11}C$]formaldehyde from [$^{11}C$] methanol beginning in 1972 (Christman, et al. (1972) Proc. Natl. Acad. Sci. USA 69:988), improved over time with new catalysts (Roeda, et al. (2003) J. Label. Comp. Radiopharm. 46:449), and quite elegantly synthesized enzymatically (Slegers, et al. (1984) J. Nuc. Med. 25:338; Svärd, et al. (1984) J. Label. Comp. Radiopharm. 21:1175; Hughes, et al. (1995) Nucl. Med. Biol. 22:105). Although these methods have been developed for synthesis of [$^{11}$C]formaldehyde from [$^{11}$C]methanol, none have been adapted to be operable in the equipment available to the majority of radiochemists.

While each of these methods has found utility, they each have disadvantages preventing more widespread use. The previous methods for the preparation of [$^{11}$C]formaldehyde have relied on the partial or the complete reduction of $^{11}CO_2$ to $^{11}CH_3OH$ followed by oxidation, as shown in reaction schemes 1.1 and 1.2.

Partial Reduction:

Complete Reduction:

Because these methods rely on a reduction step that occurs in solution, typically with lithium aluminum hydride, a reduction in specific activity occurs.

We sought to avoid these previously used routes and to make use of the widely available and gas-phase produced $^{11}CH_3I$ as the starting material for the efficient, simple production of $^{11}$C-formaldehyde. In developing the methods and materials we sought to bear in mind that for generalized utility it would be most useful if the production could be made without the need for new equipment, further bearing in mind that the reaction conditions needed to be mild and of short duration.

SUMMARY OF THE INVENTION

Synthesis of formaldehyde containing isotopes of carbon ($^{11}$C, $^{13}$C and $^{14}$C) and hydrogen (deuterium (D) and tritium (T)) are contemplated embodiments of this invention. A preferable embodiment of the present invention is the simple, efficient production of [$^{11}$C]formaldehyde ($^{11}CH_2O$) for use in the formation of $^{11}$C-labeled radiotracer compounds for positron emission tomography.

The present invention includes methods and materials for the simple, efficient production of [$^{11}$C]formaldehyde ($^{11}CH_2O$) from [$^{11}$C]methyl iodide ($^{11}CH_3I$) for use in the formation of radiotracer compounds for positron emission tomography. The methods of the invention result in the formation of $^{11}CH_2O$ from $^{11}CH_3I$ with little or no $^{11}$C isotopic dilution. The materials of the invention include oxygen nucleophiles having pendant leaving groups, and which oxygen nucleophiles are capable of displacing iodide, forming an O-methyl intermediate and, through elimination, yield formaldehyde.

In some embodiments, the methods produce in a mixture of $^{11}CH_2O$ and oligomerized $^{11}CH_2O$ adducted with the oxygen nucleophile.

An additional embodiment of the invention provides for reacting the $^{11}CH_2O$ and the oligomerized $^{11}CH_2O$ or mixtures thereof in various synthetic processes to form desirable $^{11}$C radiotracer compounds.

In one form of the invention, the methods and materials of the invention are incorporated into automated equipment available for use in the production of carbon-11 radiotracers for PET studies.

Using [$^{11}$C]methyl iodide to directly generate [$^{11}$C]formaldehyde is advantageous to previous methods for several reasons. First, $^{11}CH_3I$ is routinely produced at virtually every facility where carbon-11 compounds are synthesized. Use of [$^{11}$C]methyl iodide capitalizes on the efforts that have gone into the development of methods and equipment (now commercially available) for the gas phase synthesis for high specific-activity $^{11}CH_3I$. Each of the existing methods for [$^{11}$C]formaldehyde has relied upon a reduction step that occurs in solution, typically with lithium aluminum hydride, which often causes a reduction in specific activity avoided by gas-phase production of $^{11}CH_3I$ (Längstrom, et al. (1976) Int. J. Appl. Radiat. Isot. 27:257; Larsen, et al. (1997) Appl. Radiat. Isot. 48:153). Also, since methyl iodide is decidedly electrophilic, we suspected that we could use more mild reagents and conditions than are used for methanol oxidation. Thus, our efforts began with the simple mechanistic oxidation premise outlined in reaction scheme 1.3.

1.3

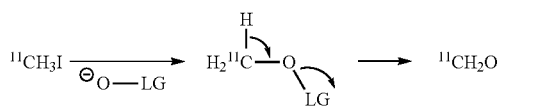

The simple mechanistic approach involves use of an oxygen nucleophile containing a pendant leaving group (LG). Nucleophilic attack by the reactive oxygen species of oxygen nucleophiles displaces the iodide from $^{11}CH_3I$ to form an intermediate having the following generalized structure (1) where LG represents a leaving group:

(1)

Hydrogen elimination results in the formation of the carbonyl bond of formaldehyde, coupled with displacement of the leaving group (LG) as depicted in reaction scheme 1.3.

The resultant $^{11}CH_2O$ may be in the form of a mixture of $CH_2O$ and oligomerized formaldehyde adducted to the leaving group, exemplified as structure (2):

(2)

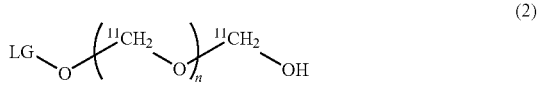

Such oligomerization is similar to the oligomerization of formaldehyde that occurs in aqueous solution (e.g., Le Botlan, et al. (1983) Anal. Chem. 55:587).

The formaldehyde/oligomer mixture can be used in a variety of reaction scenarios including reductive amination of anilines, oxime and hydrazone formation and cyclization reactions.

Synthesis of formaldehyde containing other isotopes of carbon ($^{13}$C and $^{14}$C) and hydrogen (deuterium (D) and tritium (T)) are contemplated embodiments of this invention. The $^{13}$C-labeled formaldehyde is useful as a substitute for the $^{11}$C-labeled formaldehyde when a new synthetic route is developed. The reaction intermediates and products formed using $^{13}CH_2O$ can be readily analyzed by NMR. The $^{14}$C-labeled formaldehyde can be incorporated into the radiotracer compound and then used for in vitro autoradiographic studies designed to validate in vivo imaging studies.

Deuterium- or tritium-substituted formaldehyde (*CD$_2$O or *CT$_2$O, where *C denotes an isotope of carbon) can be simply incorporated into the methods of the invention. By using D$_2$ or T$_2$ in the preparation of methane from *CO$_2$ the isotopes will then be incorporated into the methyl iodide that is made from the *CD$_4$ or *CT$_4$. Deuterium labeling has been used to enhance the utility of various PET radiotracers (e.g., Fowler, et al. 1995). Tritium labeled radiotracers can be used in vitro to validate results of imaging studies and to quantify circulating concentrations of radiotracer compounds.

DETAILED DESCRIPTION OF THE INVENTION

The methods and materials of the invention provide a simple, efficient new method for the preparation of isotopically-labeled formaldehyde from isotopically-labeled methyl iodide (e.g., C-11, C-13, C-14 separately or in combination with deuterium or tritium—hereinafter noted as *C$^§$H$_3$I where *C denotes an isotope of carbon and $^§$H denotes hydrogen, deuterium or tritium). The method makes use of existing methods for the preparation of the *C$^§$H$_3$I precursor and the methods can be readily incorporated into existing commercially available equipment typically used to create radiotracers for use in positron emission tomography (PET) procedures.

In a preferred embodiment of the invention, the methods improve and replace previous attempts to make $^{11}$CH$_2$O for use in PET procedures, which methods involved partial or complete reduction of $^{11}$CO$_2$. The methods of the present invention produce $^{11}$CH$_2$O with little if any $^{11}$C isotopic dilution, resulting in high specific activity product.

The methods make use of an oxygen nucleophile having a pendant leaving group. The methods involve the nucleophilic attack by the reactive oxygen species of the nucleophile on the carbon atom of methyl iodide, followed by hydrogen elimination and displacement of the leaving group, resulting in the formation of the formaldehyde product. In some embodiments of the method, a methylation intermediate between the oxygen nucleophile and the methyl iodide has been observed. The rate of decomposition of the intermediate resulting in the formation of formaldehyde was related to the nature of the leaving group.

In the method, gaseous methyl iodide ($^{11}$CH$_3$I) (or $^{11}$CD$_3$I or $^{11}$CT$_3$I, i.e., $^{11}$C$^§$H$_3$I), readily produced with automated systems in standard PET tracer laboratories, is incubated in a solvent with the oxygen nucleophile at temperatures ranging from about 10° C. to about 100° C., preferably between about 20° C. and 90° C., more preferably between about 20° C. and about 70° C. and most preferably between about 40° C. and about 70° C.

Reaction between the $^{11}$C$^§$H$_3$I and the oxygen nucleophile is allowed to proceed for about 1 to about 120 seconds, preferably about 20 to about 120 seconds and most preferably from about 30 seconds to about 120 seconds.

In one embodiment of the invention the starting material, $^{11}$C$^§$H$_3$I is incubated in the above conditions, in the presence of solvent with an oxygen nucleophile. Said oxygen nucleophile has a pendant leaving group.

The oxygen nucleophile having a pendant leaving group is selected from the group including inorganic oxygen nucleophiles, siloxides, sulfoxides, periodates, peroxides, hypochlorites, oxyl radical compounds, hypervalent iodine oxidants, and organic amine oxygen nucleophiles. Examples of inorganic oxygen nucleophiles are silver salts such as silver iodate, silver chromate, silver nitrate, silver nitrite, silver sulfate, and silver perchlorate. Periodates and perchlorates such as sodium periodate, sodium metaperiodate, and sodium hypochlorite are typical oxygen nucleophiles. Compounds such as 2,2,6,6-Tetramethylpiperidine-1-oxyl (TEMPO) are examples of oxyl free radical compounds that are used to oxidize alcohols to aldehydes. Hypervalent iodine oxidants, such as 12-I-5 Dess Martin periodane (1,1,1-triacetoxy-1,1-dihydro-1,2-benziodoxol-3(1H)-one) and its precursor, 10-I-4 iodinane oxide (1-hydroxy-1,2-benziodoxol-3 (1H)-one 1-oxide, i.e., o-iodoxybenzoic acid, IBX) are often used to oxidize alcohols to carbonyl compounds. Trialkylamine oxides, such as trimethylamine- and triethylamine-N-oxide and N-methylmorpholine-N-oxide, are examples, among others, of organic amine oxygen nucleophiles.

Leaving groups are well known by those skilled in the art and may include tosylates, triflates, halides, sulfides, nitrites, cyanides, and trialkyamines and quaternary ammonium cations.

Solvents useful in the method may be selected from solvents that are polar aprotic solvents, such as acetonitrile, dimethylsulfoxide, tetrahydrofuran, and dimethylformamide. In the present work, dimethylformamide was found to be an excellent solvent.

With respect to $^{11}$C isotopic dilution, the $^{11}$C:$^{12}$C ratio obtained in a typical cyclotron bombardment of N$_2$ is about 1:5000 (Fowler, et al. (1997)) (i.e., one atom of every 5,000 atoms of generated carbon is carbon-11). The immediate product of the bombardment of N$_2$ therefore is $^{11}$CO$_2$:$^{12}$CO$_2$ in a ratio of 1:5,000. The automated generation of $^{11}$C$^§$H$_3$I in the gaseous state from the carbon dioxide does not significantly change this ratio. Production of $^{11}$C$^§$H$_2$O from $^{11}$C$^§$H$_3$I with no $^{11}$C isotopic dilution would then result in formaldehyde having a $^{11}$C$^§$H$_2$O:$^{12}$C$^§$H$_2$O ratio of about 1:5,000 as well. Little or no $^{11}$C isotopic dilution with respect to the methods and materials of the invention is intended to mean generating formaldehyde having no more than about a 2- to 4-fold isotopic dilution and preferably no more than a 2-fold isotopic dilution (i.e, a $^{11}$C$^§$H$_2$O:$^{12}$C$^§$H$_2$O ratio of about 1:20,000 to about 1:5,000 and preferably a $^{11}$C$^§$H$_2$O:$^{12}$C$^§$H$_2$O ratio of about 1:10,000 to about 1:5,000).

The incorporation of the synthetic methods of the invention into commercially available PET tracer equipment is a preferred aspect of the invention. For example, the General Electric TRACERlab™ FX C Pro can be adapted to include a sealable vessel into which a stream of $^{11}$C$^§$H$_3$I can be mixed with a solvent and an oxygen nucleophile, and after an appropriate reaction time, the product can be used to label a precursor of the desired radiotracer compound through various reactions. In line high pressure liquid chromatography (HPLC) set ups can then be used to purify the radiotracer from the reaction components.

The following examples are presented to illustrate the materials, synthetic methods and utilities of the invention but are in no way intended to limit the scope of equivalent materials and methods which those of skill in the art would readily recognize may be used to accomplish the simple, efficient production of $^{11}$C$^§$H$_2$O from $^{11}$C$^§$H$_3$I, with little or no $^{11}$C isotopic dilution.

EXAMPLE 1

Oxidation of Methyl Iodide

Using $^1$H-NMR spectrometry, the reaction of sub-stoichiometric methyl iodide with a number of oxygen nucleophiles containing a pendant leaving group (LG) was examined. Many inorganic compounds were effective, but led to over oxidation. Our first lead resulting exclusively in formaldehyde was found by comparing the reaction of o-iodoxybenzoic acid (IBX, A) with methanol and methyl iodide (scheme 1.4) The common intermediate, B, was observed, which converted to formaldehyde over the course of several days.

1.4

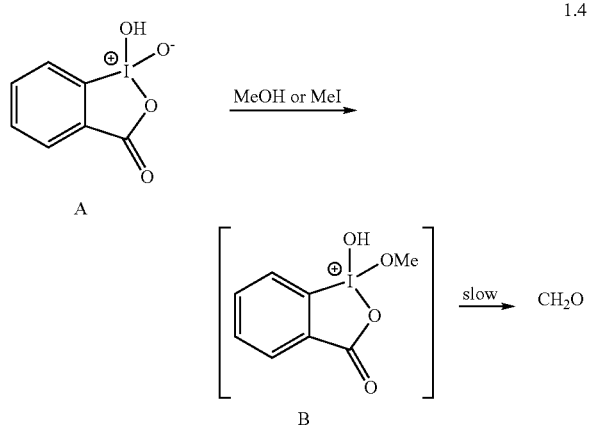

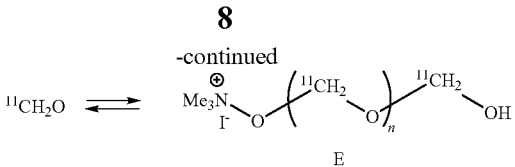

It was evident from this study that oxidation or displacement of the leaving group, rather than methylation, was rate limiting.

EXAMPLE 2

Trialkyamine-N-Oxide Oxygen Nucleophiles

To improve the reaction rate, we turned to trialkylamine-N-oxides, which we predicted would provide a better leaving group.

By reacting trimethylamine-N-oxide (TMAO) (C, below) with methyl iodide, we observed methylation (D) and subsequent formaldehyde formation immediately (as determined by the presence of a $^1$H resonance at ca. 9.5 ppm). In fact, the decomposition of solid D to formaldehyde at high temperatures had been reported nearly a century ago when the structure of TMAO was under debate (Meisenheimer, (1913) Justus Liebigs Ann. Chem. 397:273). Given excess TMAO, D underwent elimination to form formaldehyde at RT. This process occurred quantitatively at slightly elevated temperatures.

Triethylamine-N-oxide and N-methylmorpholine-N-oxide were also effective, but necessitated longer reaction times whereas pyridine-N-oxide was ineffective under all condition screened.

Upon formation, formaldehyde oligomerized (E) in the presence of TMAO giving rise to multiple methylene resonances at 4.3-4.8 ppm. This is similar to the formation of oligomers of formaldehyde that form in aqueous solutions (Le Botlan et al. (1983)).

1.5

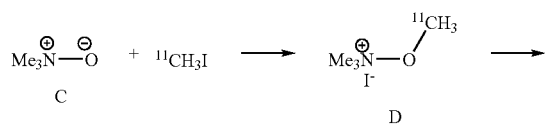

EXAMPLE 3

Lack of $^{11}$C Isotopic Dilution

We used $^{13}$CH$_3$I to determine if the use of TMAO introduced any isotopic dilution during course of the reaction and to assign all resonances resulting from methyl iodide. We found that the ratio of $^{12}$C/$^{13}$C remained 1/100 throughout the reaction, suggesting that methyl groups of TMAO would not impact the specific activity of reactions performed with $^{11}$CH$_3$I.

EXAMPLE 4

Reaction Conditions—Solvent, Time and Temperature

To test the viability of this method for the preparation of [$^{11}$C]formaldehyde, we assayed the effect of solvent, TMAO concentration, and reaction time and temperature with the dimedone precipitation method used in previous [$^{11}$C]formaldehyde reports to quantify the yield of $^{11}$CH$_2$O, (a partial list of conditions screened is given in Table 1). Briefly, an aliquot of the C-11 reaction mixture was added to carrier formaldehyde, which was subsequently precipitated as a dimedone adduct. The precipitate was separated by filtration or centrifugation and the % radioactivity in the precipitate was determined. As a control, we omitted TMAO from the reaction and performed the formaldehyde analysis, e.g. Table entry 5, and found <5% of the radioactivity was associated with the precipitate, which could be removed with washing. We found that DMF was an excellent solvent for the transformation, providing high yields of [$^{11}$C]formaldehyde in 30 to 120 seconds at only 70° C.

TABLE 1

| | | Reaction Conditions[a] | | | |
|---|---|---|---|---|---|
| Entry | Solvent | Time (sec) | TMAO (mg) | T [° C.] | Yield [%][b] |
| 1 | MeCN | 120 | 4.0 | 70 | 27 ± 7 |
| 2 | MeCN | 120 | 25.0 | 70 | 58 ± 8 |
| 3 | DMSO | 120 | 4.0 | 70 | 23 ± 7 |
| 4 | THF | 120 | 4.0 | 70 | 26 ± 4 |
| 5 | DMF | 120 | — | 70 | 3 ± 2[c] |
| 6 | DMF | 120 | 1.0 | 70 | 80 ± 2 |
| 7 | DMF | 30 | 4.0 | 70 | 72 ± 5 |
| 8 | DMF | 60 | 4.0 | 70 | 86 ± 4 |
| 9 | DMF | 120 | 4.0 | 70 | 89 ± 4 |
| 10 | DMF | 120 | 4.0 | 20 | 38 ± 6 |

[a]Reactions were performed in 300 μL of solvent with approximately 1 mCi $^{11}$CH$_3$I.
[b]Average ± standard deviation from n experiments (n = 3) based on dimedone precipitation method.
[c]Radioactivity lost from precipitate through exhaustive washing.

In DMF the amount of TMAO from 1 to 4 mg did not significantly change the yield of [$^{11}$C]formaldehyde, while in the other solvents the amount of TMAO had a significant effect.

In the same time frames, the yields of [$^{11}$C]formaldehyde were reduced in reactions run at lower temperatures. Increasing the reaction time generated yields comparable to those run at 70° C. Higher temperatures were equally effective with no over-oxidation observed.

We found the reaction to be reproducible and robust. The reaction was not sensitive to small amounts of water (up to 10 λL were added) and the dihydrate form of TMAO, which is less expensive, was an equally effective reagent. Added base was tolerated so long as it did not competitively methylate. However, the addition of acid lowered reaction yields or prevented [$^{11}$C]formaldehyde formation altogether.

EXAMPLE 5

Reactions of the $CH_2O$

In C-12 test experiments, we successfully used the formaldehyde/oligomer mixture (E) in a variety of reaction scenarios including reductive amination of anilines, oxime and hydrazone formation, and cyclization reactions.

EXAMPLE 6

Reaction of $^{11}CH_2O$

To highlight the efficacy of this mixture as no carrier added [$^{11}$C]formaldehyde and to determine specific activity, we performed a Pictet-Spengler condensation with tryptamine, reaction 1.6.

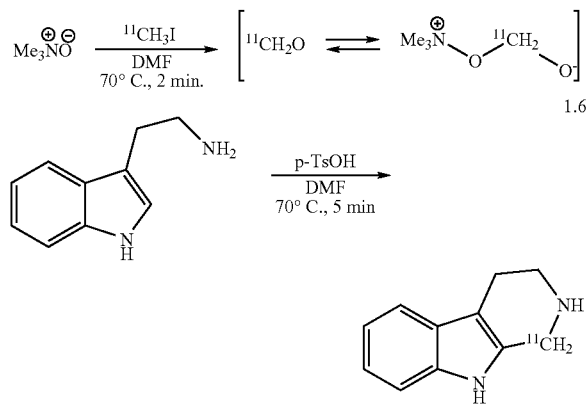

The reaction of tryptamine with the formaldehyde/oligomer mixture occurred readily under acidic conditions affording [$^{11}$C]-2,3,4,9-tetrahydro-1H-beta-carboline in 65-75% radiochemical yield. The product was isolated by semi-preparative HPLC using a C18 column and the mass was determined by absorbance at 254 nm. Using a portion of [$^{11}$C] methyl iodide from a clinical production run, we determined that the product had a specific activity of 3 Ci/µmol. The clinical product generally has a specific activity of 4.5 Ci/µmol. We attribute the slightly reduced specific activity of the product of the present synthesis to be related to the presence of formaldehyde which may be present in many chemicals and solvents. For very high specific activity syntheses, formaldehyde should be rigorously excluded from all materials used in the reactions.

To further verify TMAO itself does not contribute formaldehyde to the reaction solution, we ran two critical negative control reactions under the same preparative-scale conditions. First, we omitted methyl iodide and found no product formation. In the second, TMAO was omitted and no carbon 11 labeled product was obtained.

EXAMPLE 7

General Procedure

The general procedure for conversion of $^{11}C^sH_3I$ to $^{11}C^sH_2O$ suitable for incorporation into an automated system is as follows:

A mixture of trimethylamine-N-oxide or its hydrate (4 mg) and DMF (300 µL) cooled to −40° C. was used to capture $^{11}CH_3I$ produced using the PETtrace MeI Microlab (GE Medical Systems, Milwaukee, Wis.). To effect the reaction, the sealed vessel was heated to 70° C. for 2 minutes and the cooled in an ice bath for the analysis of reaction products. Alternatively this reaction could be carried out in the gas phase for example by incorporation of the trialkyamine-N-oxide on a solid support and reaction with the $^{11}CH_3I$ in the gas phase.

For practical applications, such as the above incorporation of the $^{11}C^sH_2O$ into a desired radiotracer compound, the reaction vessel may not require chilling. Instead, for example, the various product precursors and reagents (e.g., acids/bases/catalysts) could be added directly to the 70° C. reaction vessel after the 2 minute reaction to form formaldehyde. It is likewise possible that $^{11}C^sH_2O$ could be revolatilized for reaction in the gas phase.

The simple and easily automated method for production of isotopically labeled formaldehyde can be performed with commercially available, inexpensive trimethylamine-N-oxide under mild conditions with little or no $^{11}C$ isotopic dilution. It is anticipated that if made readily available through these methods reactions such as electrophilic aromatic substitutions, Mannich-type condensations, and cyclization reactions will be developed for incorporating $^{11}C$ and other isotopes of carbon and deuterium and tritium into a wide variety of PET radiotracer compounds.

It is anticipated that the skilled artisan will readily recognize equivalent variations of the detailed exemplifications described herein which can be used to accomplish the conversion of $^{11}C^sH_3I$ to $^{11}C^sH_2O$.

The invention claimed is:

1. A method for the production of [$^{11}$C]-formaldehyde ($^{11}CH_2O$) comprising:
   a) providing [$^{11}$C]-methyl iodide ($^{11}CH_3I$);
   b) reacting $^{11}CH_3I$ of step a) with an oxygen nucleophile, said nucleophile containing a pendant leaving group (LG), under conditions appropriate for formation of a methylation intermediate between said nucleophile and $^{11}CH_3I$; and
   c) allowing said intermediate to decompose to form $^{11}CH_2O$.

2. The method according to claim 1 wherein $^{11}CH_3I$ is provided in a gaseous state.

3. The method according to claim 2 wherein gaseous $^{11}CH_3I$ is produced through iodination of [$^{11}$C]-methane ($^{11}CH_4$).

4. The method according to claim 3 wherein $^{11}CH_4$ is produced by reduction of [$^{11}$C]-carbon dioxide ($^{11}CO_2$).

5. The method according to claim 4 wherein $^{11}CO_2$ is produced by proton irradiation of nitrogen gas ($N_2$).

6. The method according to claim 3 wherein $^{11}CH_4$ is produced by irradiation of nitrogen gas ($N_2$) in the presence of molecular hydrogen ($H_2$).

7. The method according to claim 1 wherein the oxygen nucleophile is selected from the group consisting of inorganic oxygen nucleophiles, siloxides, sulfoxides, periodates, peroxides, hypochlorites, oxyl radical compounds, hypervalent iodine oxidants and organic amine oxygen nucleophiles.

8. The method according to claim 7 wherein the oxygen nucleophile is a hypervalent iodine oxidant.

9. The method according to claim 8 wherein the hypervalent iodine oxidant is either 12-I-5 Dess Martin periodane (1,1,1-triacetoxy-1,1-dihydro-1,2-benziodoxol-3(1H)-one) or 10-I-4 iodinane oxide (1-hydroxy-1,2-benziodoxol-3(1H)-one 1-oxide, i.e., o-iodoxybenzoic acid, IBX).

10. The method according to claim 9 wherein the hypervalent iodine oxidant is 10-I-4 iodinane oxide (1-hydroxy-1,2-benziodoxol-3(1H)-one 1-oxide, i.e., o-iodoxybenzoic acid, IBX).

11. The method according to claim 7 wherein the oxygen nucleophile is a trialkylamine-N-oxide.

12. The method according to claim 11 wherein said trialkylamine-N-oxide is selected from the group consisting of trimethylamine-N-oxide, triethylamine-N-oxide and N-methylmorpholine-N-oxide.

13. The method according to claim 12 wherein said trialkylamine-N-oxide is trimethylamine-N-oxide (TMAO).

14. The method according to claim 11 wherein at least some of said $^{11}CH_2O$ of step c) forms an oligomer.

15. The method according to claim 13 wherein at least some of said $^{11}CH_2O$ of step c) forms an oligomer.

16. The method according to claim 11 wherein the reaction of step b) is carried out in the presence of excess trialkylamine-N-oxide.

17. The method according to claim 1 wherein the reaction of step b) is carried out in the presence of a solvent.

18. The method according to claim 17 wherein the solvent is a polar aprotic solvent.

19. The method according to claim 18 wherein the solvent is selected from the group consisting of acetonitrile, dimethoxysulfate, tetrahydrofuran and dimethylformamide.

20. The method according to claim 19 wherein the solvent is dimethylformamide.

21. The method according to claim 20 wherein the oxygen nucleophile is trialkylamine-N-oxide.

22. The method according to claim 11 wherein steps b) and c) are allowed to proceed for a total of about 1 to about 120 seconds.

23. The method according to claim 22 wherein steps b) and c) are allowed to proceed for a total of about 20 to about 120 seconds.

24. The method according to claim 23 wherein steps b) and c) are allowed to proceed for a total of about 30 to about 120 seconds.

25. The method according to claim 11 wherein the reaction of steps b) and steps c) are carried out at a temperature range from about 10° C. to about 100° C.

26. The method according to claim 25 wherein said temperature range is from about 20° C. to about 90° C.

27. The method according to claim 26 wherein said temperature range is from about 20° C. to about 80° C.

28. The method according to claim 27 wherein said temperature range is from about 20° C. to about 70° C.

29. The method according to claim 28 wherein said temperature range is from about 40° C. to about 70° C.

30. A method for the production of high specific activity [$^{11}C$]-formaldehyde ($^{11}CH_2O$) comprising the steps of:
a) providing $^{11}CH_3I$ in a gaseous state;
b) reacting said $^{11}CH_3I$ with an excess of a trialkyamine-N-oxide nucleophile in the presence of a solvent at a temperature range of from about 20° C. to about 70° C. for a period of time between 30 seconds and 120 seconds so as to form an intermediate between the nucleophile and the $^{11}CH_3I$; and
c) allowing said intermediate to decompose to form $^{11}CH_2O$.

31. The method of claim 30 wherein the trialkyamine-N-oxide is trimethylamine-N-oxide.

32. The method of claim 31 wherein the decomposition results in the formation of at a mixture of $^{11}CH_2O$ and an oligomer of $^{11}CH_2O$.

33. The method of any one of claims 1, 13, or claim 30 further including reacting the resultant $^{11}CH_2O$ to form $^{11}C$-labeled compounds for use as radiotracers for positron emission tomography (PET).

34. The method of claim 33 wherein the reactions are chosen from the group consisting of reductive methylations, ring-closure reactions, electrophilic aromatic substitutions, Mannich-type condensations, and cyclization reactions.

35. The method of claim 33 wherein reaction of the $^{11}CH_2O$ is catalyzed by an enzyme catalyst.

36. The method of any one of claims 14, 15, or 32 further including reacting the resultant $^{11}CH_2O/^{11}CH_2O$-oligomer mixture to form of 11C- labeled compounds for use as radiotracers for positron emission tomography (PET).

37. The method of claim 36 wherein the reactions are chosen from the group consisting of reductive methylations, ring-closure reactions, electrophilic aromatic substitutions, Mannich-type condensations, and cyclization reactions.

38. The method of claim 36 wherein reaction of the $^{11}CH_2O$ is catalyzed by an enzyme catalyst.

39. $^{11}C$-labeled formaldehyde ($^{11}CH_2O$) formed by the method comprising the steps of:
a) providing [$^{11}C$]-methyl iodide ($^{11}CH_3I$);
b) reacting $^{11}CH_3I$ of step a) with an oxygen nucleophile, said nucleophile containing a pendant leaving group (LG), under conditions appropriate for formation of a methylation intermediate between said nucleophile and $^{11}CH_3I$; and
c) allowing said intermediate to decompose to form $^{11}CH_2O$.

40. High specific activity $^{11}C$-labeled formaldehyde ($^{11}CH_2O$) prepared by a method comprising the steps of:
a) providing $^{11}CH_3I$ in a gaseous state;
b) reacting said $^{11}CH_3I$ with an excess of a trialkyamine-N-oxide nucleophile in the presence of a solvent at a temperature range of about 20° C. to about 70° C. for a period of time between 30 seconds and 120 seconds so as to form an intermediate between the nucleophile and the $^{11}CH_3I$; and
c) allowing said intermediate to decompose to form $^{11}CH_2O$.

41. A method for the production of radiolabeled-formaldehyde (*$C^{517}H_2O$, wherein *C denotes $^{11}C$, $^{13}C$ or $^{14}C$ and $^{517}H$ denotes hydrogen (H), deuterium (D) or tritium (T)) comprising:
a) providing radiolabeled-methyl iodide (*$C^{517}H_3I$);
b) reacting *$C^{517}H_3I$ of step a) with an oxygen nucleophile, said nucleophile containing a pendant leaving group (LG), under conditions appropriate for formation of a methylation intermediate between said nucleophile and *$C^{517}H_3I$; and
c) allowing said intermediate to decompose to form *$C^{517}H_2O$.

42. The method according to claim 41 wherein *$C^{§}H_3I$ is provided in a gaseous state.

43. The method according to claim 42 wherein gaseous *C$^\S$H$_3$I is produced through iodination of radiolabeled methane (*C$^\S$H$_4$).

44. The method according to claim 43 wherein *C$^\S$H$_4$ is produced by reduction of radio-carbon labeled carbon dioxide (*CO$_2$).

45. The method according to claim 43 wherein $^{11}$C$^\S$H$_4$ is produced by irradiation of nitrogen gas (N$_2$) in the presence of molecular hydrogen (H$_2$), molecular deuterium (D$_2$) or molecular tritium (T$_2$).

46. The method of claim 41 further including reacting the resultant *C$^\S$H$_2$O to form radio-labeled compounds for use as radiotracers for positron emission tomography (PET), nuclear magnetic resonance, magnetic resonance imaging, scintillation counting, and autoradiography.

47. The method of claim 46 wherein the reactions are chosen from the group consisting of reductive methylations, ring-closure reactions, electrophilic aromatic substitutions, Mannich-type condensations, and cyclization reactions.

48. The method of claim 46 wherein reaction of the *C$^\S$H$_2$O is catalyzed by an enzyme catalyst.

49. $^{11}$C-labeled formaldehyde ($^{11}$CH$_2$O) having a $^{11}$C:$^{12}$C ratio between 1:5,000 and 1:20,000 formed by the method comprising the steps of:
   a) providing [$^{11}$C]-methyl iodide ($^{11}$CH$_3$I);
   b) reacting $^{11}$CH$_3$I of step a) with an oxygen nucleophile, said nucleophile containing a pendant leaving group (LG), under conditions appropriate for formation of a methylation intermediate between said nucleophile and $^{11}$CH$_3$I; and
   c) allowing said intermediate to decompose to form $^{11}$CH$_2$O.

50. High specific activity $^{11}$CH$_2$O having a $^{11}$C:$^{12}$C ratio between 1:5,000 and 1:10,000 prepared by a method comprising the steps of:
   a) providing $^{11}$CH$_3$I in a gaseous state;
   b) reacting said $^{11}$CH$_3$I with an excess of a trialkyamine-N-oxide nucleophile in the presence of a solvent at a temperature range of about 20° C. to about 70° C. for a period of time between 30 seconds and 120 seconds so as to form an intermediate between the nucleophile and the $^{11}$CH$_3$I; and
   c) allowing said intermediate to decompose to form $^{11}$CH$_2$O.

51. Radiolabeled-formaldehyde (*C$^\S$H$_2$O), wherein *C denotes $^{11}$C, $^{13}$C or $^{14}$C and $^{517}$H denotes hydrogen (H), deuterium (D) or tritium (T), said radiolabeled-formaldehyde having little or substantially no isotopic dilution of *C, formed by the method comprising the steps of:
   a) providing radiolabeled methyl iodide (*C$^{517}$H$_3$I);
   b) reacting *C$^\S$H$_3$I of step a) with an oxygen nucleophile, said nucleophile containing a pendant leaving group (LG), under conditions appropriate for formation of a methylation intermediate between said nucleophile and *C$^{517}$H$_3$I; and
   c) allowing said intermediate to decompose to form *C$^{517}$H$_2$O.

* * * * *